United States Patent
Hart (10) Patent No.: US 6,254,571 B1
(45) Date of Patent: *Jul. 3, 2001

(54) REMOTE CLOT MANAGEMENT

(75) Inventor: Charles C. Hart, Huntington Beach, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/171,268
(22) PCT Filed: Apr. 14, 1997
(86) PCT No.: PCT/US97/06296
  § 371 Date: Oct. 14, 1998
  § 102(e) Date: Oct. 14, 1998
(87) PCT Pub. No.: WO97/38631
  PCT Pub. Date: Oct. 23, 1997

Related U.S. Application Data
(60) Provisional application No. 60/015,582, filed on Apr. 18, 1996.

(51) Int. Cl.⁷ .................................................. A61M 29/00
(52) U.S. Cl. ........................................... 604/107; 606/194
(58) Field of Search .................................... 604/22, 27, 35, 604/48, 96, 101, 104–109, 266, 267, 264, 523, 528; 606/191, 192, 194, 198, 200, 159, 167, 170, 127, 128; 600/564, 565, 569, 570, 571, 572

(56) References Cited

U.S. PATENT DOCUMENTS

| | | |
|---|---|---|
| 3,435,826 | 4/1969 | Fogarty . |
| 3,467,101 | 9/1969 | Fogarty et al. . |
| 3,896,815 | 7/1975 | Fettel et al. . |
| 3,978,863 | 9/1976 | Fettel et al. . |
| 3,996,938 | 12/1976 | Clark, III . |
| 4,089,506 | 5/1978 | Blake . |
| 4,650,466 | 3/1987 | Luther . |
| 4,885,003 | * 12/1989 | Hillstead ............................... 604/107 |
| 4,921,484 | * 5/1990 | Hillstead ............................... 604/104 |
| 4,950,238 | 8/1990 | Sullivan . |
| 4,979,939 | * 12/1990 | Shiber .................................. 606/159 |
| 5,074,871 | 12/1991 | Groshong . |
| 5,135,484 | * 8/1992 | Wright ................................. 604/101 |
| 5,152,771 | 10/1992 | Sabbaghian et al. . |
| 5,192,290 | 3/1993 | Hilal . |
| 5,246,445 | 9/1993 | Yachia et al. ..................... 604/104 X |
| 5,279,546 | * 1/1994 | Mische et al. ....................... 604/101 |
| 5,279,565 | 1/1994 | Klein et al. . |
| 5,282,484 | 2/1994 | Reger . |
| 5,284,486 | 2/1994 | Kotula et al. . |
| 5,320,604 | 6/1994 | Walker et al. . |

(List continued on next page.)

FOREIGN PATENT DOCUMENTS

| | | |
|---|---|---|
| 0 448 859 | 2/1991 | (EP) . |
| 448859 | * 10/1991 | (EP) .................................... 606/159 |
| 91/02494 | 3/1991 | (WO) . |

*Primary Examiner*—Anhtuan T. Nguyen
(74) *Attorney, Agent, or Firm*—Richard L. Myers, Esq.

(57) ABSTRACT

An expandable intraluminal catheter is used for removing occlusive material from a body passage. The catheter includes a handle having both a proximal handle end and a distal handle end. Attached to the distal handle end is an elongate tubular body, which includes a proximal body end and a distal body end. The elongate tubular body further includes a lumen between the proximal body end and the distal body end. A number of expandable segments are disposed on the elongate tubular body near the distal body end. These expandable segments can be mechanically activated by a user when the distal body end is within a blood vessel, to thereby isolate and partition occlusive material within the blood vessel. The isolated and partitioned occlusive material within the blood vessel can then be removed.

22 Claims, 7 Drawing Sheets

U.S. PATENT DOCUMENTS

| | | |
|---|---|---|
| 5,370,653 | 12/1994 | Cragg . |
| 5,397,307 * | 3/1995 | Goodin .................................. 604/101 |
| 5,411,509 | 5/1995 | Hilal . |
| 5,415,636 * | 5/1995 | Forman ................................ 604/101 |
| 5,423,744 * | 6/1995 | Gencheff et al. .................... 604/101 |
| 5,674,198 * | 10/1997 | Leone .................................. 604/101 |
| 5,769,871 * | 6/1998 | Mers Kelly et al. ................ 606/159 |
| 5,827,304 * | 10/1998 | Hart ..................................... 604/101 |

\* cited by examiner

REMOTE CLOT MANAGEMENT

This application claims benefit to U.S. provisional application 60/015582 filed 4/18/1996.

BACKGROUND OF THE INVENTION

1. Field of the Invention

The present invention relates generally to embolectomy and thrombectomy devices for manipulating and treating thrombus and clots in the vascular system and, more particularly, to expandable intraluminal catheters for removing occlusive materials from body passages.

2. Description of Related Art

Expanding diameter catheters are commonly used in surgical procedures. A well-known mechanism for expanding the diameter of the catheter is inflation. These balloon-type embolectomy catheters are disclosed in U.S. Pat. No. 3,435,826, U.S. Pat. No. 3,467,101, and U.S. Pat. No. 5,320,604 for use in removing blood clots and thrombus from blood vessels. In addition to balloon-type embolectomy catheters, other mechanisms have been proposed by the prior art in an attempt to improve the procedure of removing clots and thrombus or plaque from blood vessels. U.S. Pat. No. 5,282,484 and U.S. Pat. No. 5,284,486 disclose a catheter having rotating blades. U.S. Pat. No. 5,370,653 discloses a catheter having a brush for removal of material from a blood vessel. U.S. Pat. No. 5,192,290, which is assigned to the assignee of the present invention, discloses a catheter having an expanding elastomeric foam.

All of these prior art embolectomy catheters have intrinsic problems and complications connected with use in delicate blood vessels, regardless of whether balloons, blades, or brushes are used. Since a balloon must be inflated to relatively high pressure in order to ensure proper results, the balloon may rupture or transmit excessive force to the delicate blood vessel. Sclerotic lesions, for example, may occur at sites where the intimal lining of the vessel has been damaged. Blades or brushes can cause extensive damage to the fragile lining of the delicate blood vessel, as well. An elastomeric foam member, such as that disclosed in U.S. Pat. No. 5,192,290, provides a mechanical activation of the expansion means. Although this mechanical activation provides a safety measure by giving the user a tactile feel, the elastomeric foam expansion member does not have the removal capabilities of the above-mentioned balloons, blades, and brushes.

Another problem commonly shared by all of the prior art embolectomy catheters stems from a removal method which is inherently engineered into these devices. A common principle is implemented by each of the prior art devices. Specifically, the expanding members of these prior art devices are advanced beyond the occlusive material to be removed or treated in the blood vessel, and the occlusive material is then forced as a whole along a retrieval path through the blood vessel to a collection site. If the occlusive material is well-attached to the blood vessel wall, the shear forces required to dislodge this material may be damaging to the blood vessel. Since the expanding member basically contacts a perimeter portion of the occlusive material and pushes this material through the vessel to the collection site, a resulting compression of the occlusive material often results. This compression may necessitate the application of additional, excessive force for the removal of the occlusive material, resulting in further damage to the delicate intimal lining of the blood vessel.

SUMMERY OF THE INVENTION

The expansion member of the intraluminal catheter of the present invention harnesses a mechanical activation of the expansion member, and thus does not suffer from the problems associated with prior art balloons, blades, and brushes. This mechanical activation of the expansion member provides the user with a tactile feel. Additionally, the expandable intraluminal catheter of the present invention does not rely on the removal mechanism of the prior art. Specifically, the expandable intraluminal catheter of the present invention does not contact and push only the outer perimeter of the occlusive material in the blood vessel. The expandable intraluminal catheter of this invention contacts the occlusive material along the entire length of the occlusive material within the blood vessel to thereby minimize the compression effect suffered by the prior art. The resulting force required to dislodge or mobilize the occlusive material at any one point within the blood vessel is significantly reduced, since compression is reduced and the mobilizing force is distributed over a large surface area. Since the occlusive material is contacted, and partitioned, at a number of points along the length of the occlusive material within the blood vessel, a risk that the occlusive material may be lost, left behind, or swept into the flow of the blood vessel is also reduced.

The expandable intraluminal catheter of the present invention is able to capture, manipulate, and mobilize thrombus and clots in the vascular system. The expandable intraluminal catheter further provides for the introduction of lysing agents, for example, specifically to, and only to, the affected site. The expandable intraluminal catheter further facilitates aspiration of the lysing agents from the affected site.

The expandable intraluminal catheter is used for removing occlusive material from a body passage. The catheter includes a handle having both a proximal handle end and a distal handle end. Attached to the distal handle end is an elongate tubular body, which includes a proximal body end and a distal body end. The elongate tubular body further includes a lumen between the proximal body end and the distal body end.

A number of expandable segments are disposed on the elongate tubular body near the distal body end. The expandable segments include a proximal expandable segment, a distal expandable segment, and at least one intermediate expandable segment. These expandable segments can be mechanically activated by a user when the distal body end is within a blood vessel to first radially expand the distal expandable segment and the proximal expandable segment. Subsequently, the at least one intermediate expandable segment can be expanded. The expansion of the distal expandable segment and the proximal expandable segment allows the user to isolate the occlusive material, and the subsequent expansion of the at least one intermediate expandable segment allows the user to partition the occlusive material to thereby prepare the occlusive material for removal from the body passage. The isolated and partitioned occlusive material within the body passage can then be removed.

The mechanism for mechanically activating the expandable segments includes a wire disposed within the lumen of the elongate tubular body. A proximal end of the wire is connected to the proximal handle end, and a distal end of the wire is connected to the distal body end. This connection of the wire between the handle and the distal body end fixes the length therebetween. An actuator, connected to the proximal body end, can be actuated by the user to move the proximal body end toward the relatively stationary distal body end. This movement results in an expansion of the expandable segments. Similarly, the user can reverse the direction of the actuator to increase the distance between the proximal body end and the distal body end to thereby decrease the diameters of the expandable segments. The distal expandable segment and the proximal expandable segment, when expanded, have greater diameters than the at least one intermediate expandable segment, when expanded. The greater diameters of the distal expandable segment and the proximal expandable segment allow a user to isolate an occlusive material between the distal expandable segment and the proximal expandable segment, before the at least one intermediate expandable segment is actuated to partition the occlusive material. The isolation of the occlusive material, between the distal expandable segment and the proximal expandable segment, before the partitioning of the occlusive material, substantially prevents portions of the occlusive material from escaping from between the distal expandable segment and the proximal expandable segment and, consequently, allows for a substantially complete removal of the occlusive material from the body passage.

These expandable segments may be formed of a tubular woven, braided, or meshed material having tiny apertures therein. The distal expandable segment and the proximal expandable segment are preferably covered with non-permeable dispersion coatings. When the expandable segments are activated, the small apertures in the at least one intermediate expandable segment become larger to thereby allow for liquids or small particles to pass therethrough. Thus, solvents or other medications may be administered through the lumen of the expandable intraluminal catheter, to thereby exit through the apertures of the at least one intermediate expandable segment. Suction may also be applied through the lumen to draw fluids back through the apertures. This suction may aspirate, desiccate, or in other ways mechanically attach portions of chemically treated occlusive material to the at least one expandable segment to thereby facilitate removal of the occlusive material from the blood vessel. The non-permeable dispersion coatings on the distal expandable segment and the proximal expandable segment prevent the solvents, medications, fluids, and materials from escaping from the isolated treatment area, which is defined between the distal expandable coated segment and the proximal expandable coated segment.

The mechanical activation of the plurality of expandable segments, in addition to providing a tactile feel to the user, provides an expansion mechanism which has a relatively smooth outer surface for non-destructive insertion into the blood vessel. Subsequently, the mechanical activation of the plurality of expandable segments provides relatively rigid enlarged-diameter segments for removal of the occlusive material from the blood vessel. According to another feature of the present invention, an expandable distal member, formed of elastomeric foam or a balloon, can be placed at the distal body end of the expandable intraluminal catheter tube to further facilitate effective removal of the occlusive material from the blood vessel.

The present invention, together with additional features and advantages thereof, may best be understood by reference to the following description taken in connection with the accompanying illustrative drawings.

DETAILED DESCRIPTION OF THE PROFFERED EMBODIMENTS

Figure 1A:
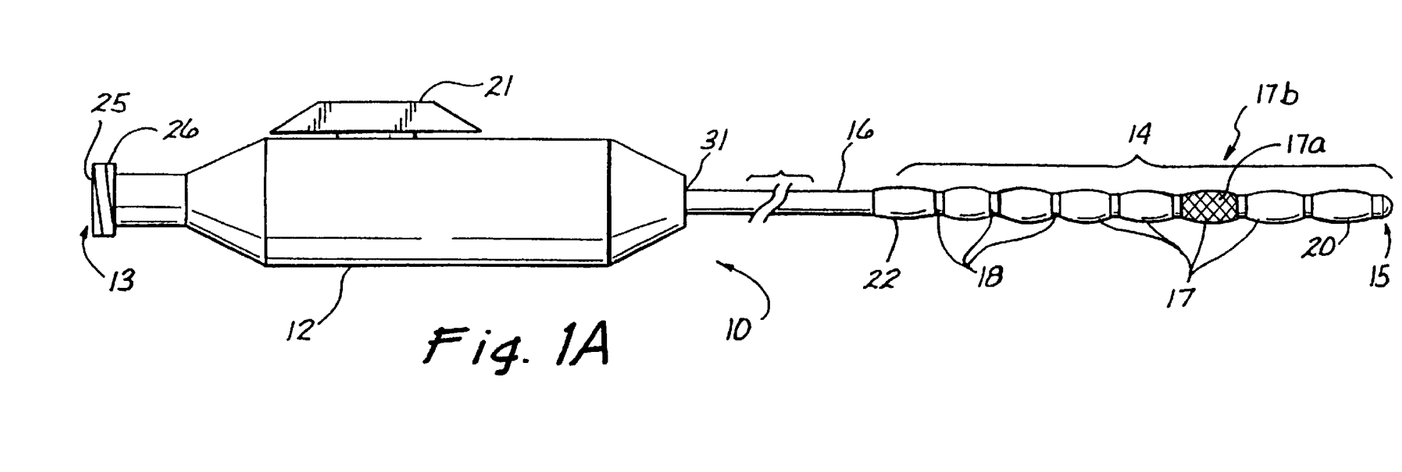
FIG. 1A is a side elevation view of the expandable intraluminal catheter of a presently preferred embodiment in an undeployed configuration.
Figure 1B:
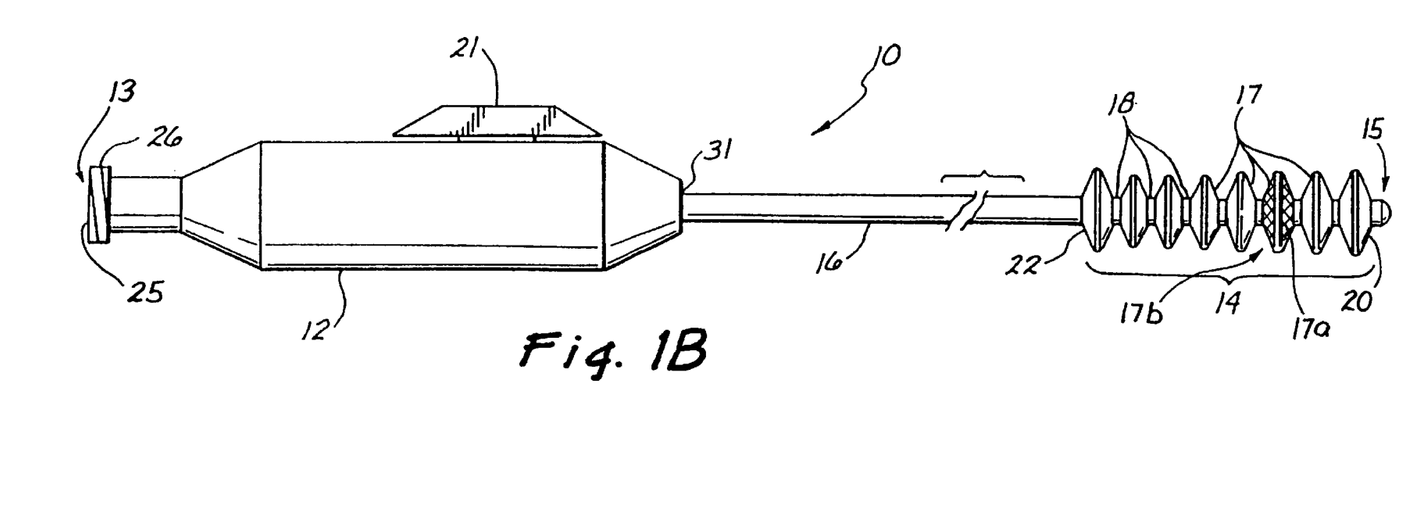
FIG. 1B is a side elevation view of the expandable intraluminal catheter of the presently preferred embodiment in a deployed or expanded configuration.

An expandable intraluminal catheter of a presently preferred embodiment is illustrated in FIG. 1 and designated generally by the reference numeral 10. The expandable intraluminal catheter 10 comprises a handle 12 and an elongate tubular body 16. The elongate tubular body 16 fits into an aperture 31 of the handle 12. A segmented distal portion 14 is located near the distal end 15 of the elongate tubular body. This segmented distal portion 14 preferably comprises a number of expandable segments 17 separated by a number of non-expandable segments 18. Each expandable segment 17 preferably comprises a tubular woven, braided, or meshed materials having aperatures 17a, as shown by a single segment 17b in FIGS. 1A and 1B.

A distal expandable segment 20 and a proximal expandable segment 22 are preferably configured to have greater lengths, measured along a length of the elongate tubular body 16, than the other expandable segments on the segmented distal portion 14. As a result of these greater lengths the distal expandable segment 20 and the proximal expandable segment 22 are first to expand, as presently embodied. Additionally, the distal expandable segment 20 and the proximal expandable segment 22, when expanded, have greater diameters than the other expandable segments on the segmented distal portion 14, when expanded.

The preferred expanding sequence and the greater diameters of the distal expandable segment 20 and the proximal expandable segment 22 allow a user to isolate an occlusive material between the distal expandable segment 20 and the proximal expandable segment 22, before the other expandable segments on the segmented distal portion 14 are subsequently actuated to partition the occlusive material. The isolation of the occlusive material, between the distal expandable segment 20 and the proximal expandable segment 22, before the partitioning of the occlusive material, substantially prevents portions of the occlusive material from escaping from between the distal expandable segment 20 and the proximal expandable segment 22. Consequently, a substantially complete removal of the occlusive material from the body passage can be achieved. In one embodiment, the segmented distal portion 14, after isolating and capturing an occlusive material, may be withdrawn into a sheath (not shown) and the sheath subsequently withdrawn from the body passage.

Each of the non-expandable segments preferably comprises a semi-rigid plastic tubing. The handle 12 is configured to be gripped by the hand of a user, and the actuator 21 is movable between a reverse position shown in FIG. 1A and a forward position shown in FIG. 1B. An opening or port 25 is located at the proximal end of the handle 12. This opening 25 preferably comprises a luer-type locking hub 26. The distal expandable segment 20 and the proximal expandable segment 22, when expanded, snugly contact the inner wall of a body passage. As presently embodied, the distal expandable segment and the proximal expandable segment comprise non-permeable dispersion coatings. As a result of these non-permeable dispersion coatings, the distal expandable segment 20 and the proximal expandable segment 22, when expanded within the body passage, effectively create a sealed treatment area therebetween. A thrombus or clot which is isolated between the distal expandable segment 20 and the proximal expandable segment 22 can be treated with lysing agents, for example, which are introduced through the luer-type locking hub 26 into the body passage via apertures in the other radially-expanded segments on the segmented distal portion 14. The non-permeable dispersion coatings on the distal expandable segment 20 and the proximal expandable segment 22 prevent solvents, medications, fluids, and materials from escaping from the isolated treatment area, which is defined between the distal expandable coated segment 20 and the proximal expandable coated segment 22. The treatments to the occlusive material within the isolated treatment area can thus be applied specifically to, and only to, the affected site within the isolated treatment area. The expandable intraluminal catheter of the present invention further facilitates aspiration of the lysing agents, for example, from the isolated treatment area through the luer-type locking hub 26 via apertures in the radially-expanded segments between the distal expandable coated segment 20 and the proximal expandable coated segment 22.

As shown in FIG. 1B, movement of the actuator 21 into the forward position results in an expansion of the expandable segments 17. As presently preferred, the distal expandable segment 20 and the proximal expandable segment 22 are first radially expanded and, subsequently, the other radially-expanded segments on the segmented distal portion 14 are expanded. The expansion of the distal expandable segment 20 and the proximal expandable segment 22 allows the user to isolate the occlusive material. The subsequent expansion of the other radially-expanded segments on the segmented distal portion 14 allows the user to partition the occlusive material to thereby prepare the occlusive material for treatment and removal from the body passage.

As each expandable segment 17 radially expands, a corresponding width of that expandable segment, measured in the direction of a longitudinal axis of the elongate tubular body 16, decreases. The non-expandable segments 18 do not radially expand upon movement of the actuator 21 into the forward position and, further, do not decrease in width, measured along the longitudinal axis of the elongate tubular body 16.

Figure 2A:
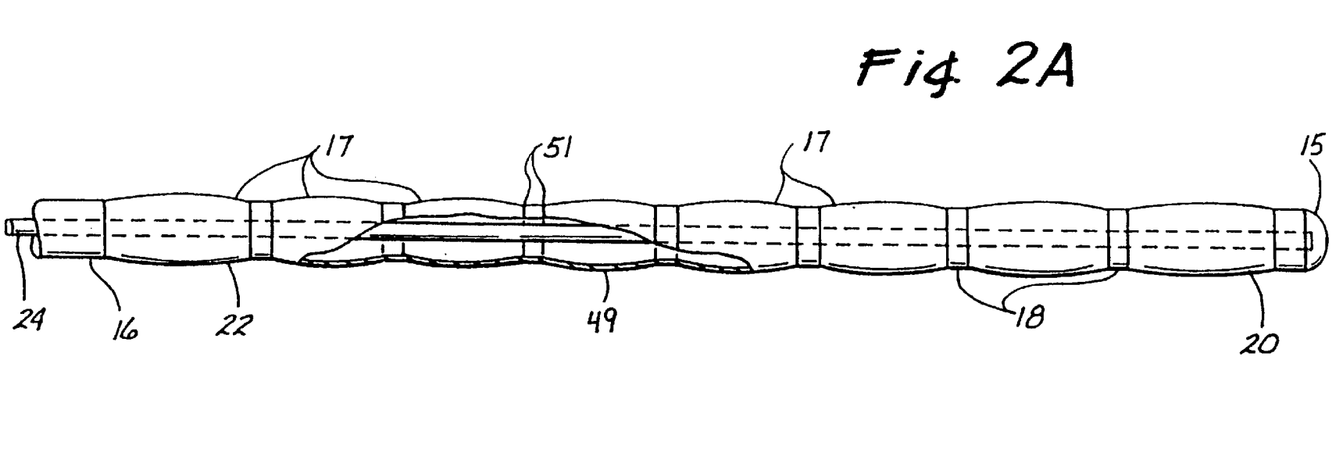
FIG. 2A is a partial cross-sectional view of the distal portion of the expandable intraluminal catheter in an undeployed configuration, according to the presently preferred embodiment.
Figure 2B:
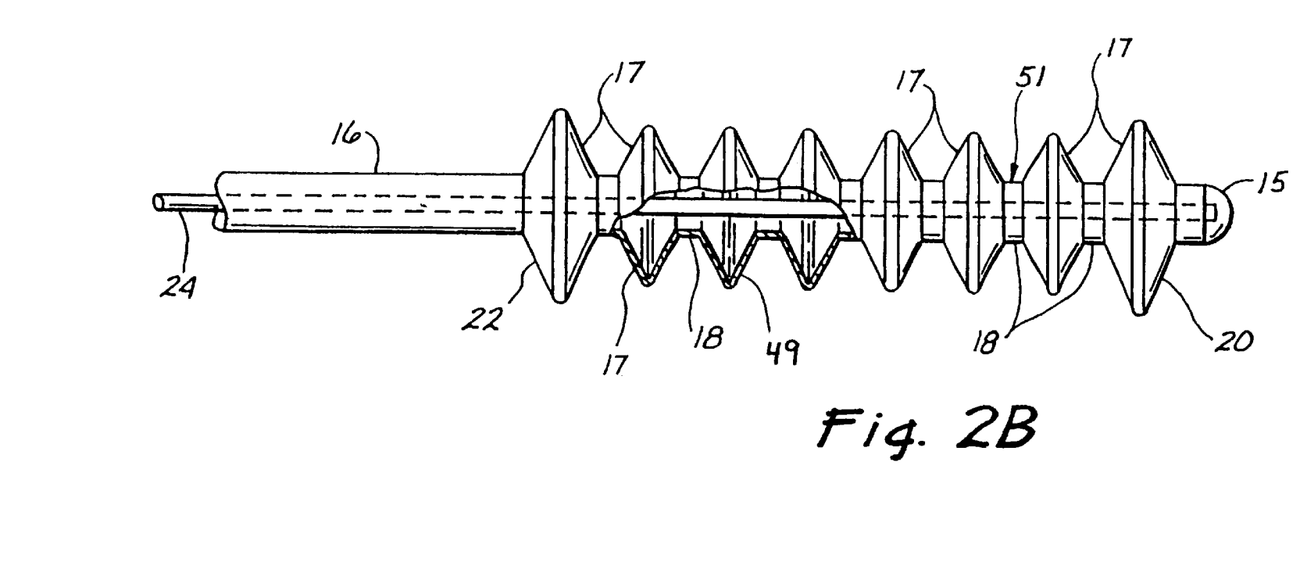
FIG. 2B is a partial cross-sectional view of the distal portion of the expandable intraluminal catheter in an expanded configuration, according to the presently preferred embodiment.

FIG. 2A illustrates a closer view of the segmented distal portion 14 of the elongate tubular body 16 in the non-activated configuration. In the presently preferred embodiment, the expandable segments 17 and the non-expandable segments 18 are formed of different materials, but comprise a same wall 49. The expandable segments 17 and the non-expandable segments 18 are fused together at fusion points 51 along the longitudinal axis of the tubular elongate body 16. Alternatively, a single expandable material may be fused at the fusion points 51, or non-expandable bands may be placed around the wall 49 to form the non-expandable segments 18. In the presently preferred embodiment, the locations of the fusion points 51 along the longitudinal axis of the elongate tubular body 16 are selected to correspond to predetermined expansion ratios. Each of the fusion points 51 is thus positioned to yield a deployed cone-shaped expandable segment 17 (FIG. 2B) of a predetermined diameter and circumference. According to the presently preferred embodiment, the braided material which comprises the wall 49 has a characteristic which causes the expandable segments 17 having greater lengths to expand before the expandable segments 17 having lesser lengths.

Figure 3A:
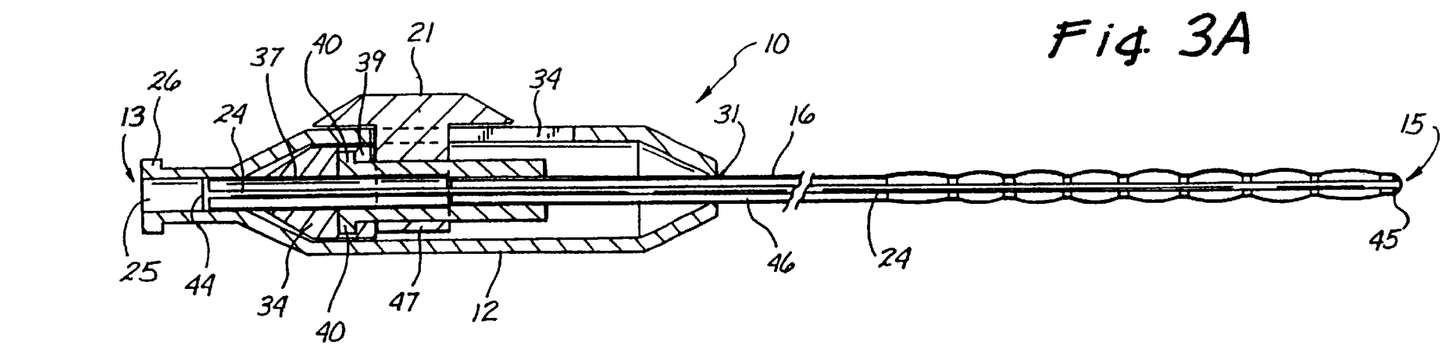
FIG. 3A is a cross-sectional view of the expandable intraluminal catheter in an undeployed condition, according to the presently preferred embodiment.
Figure 3B:
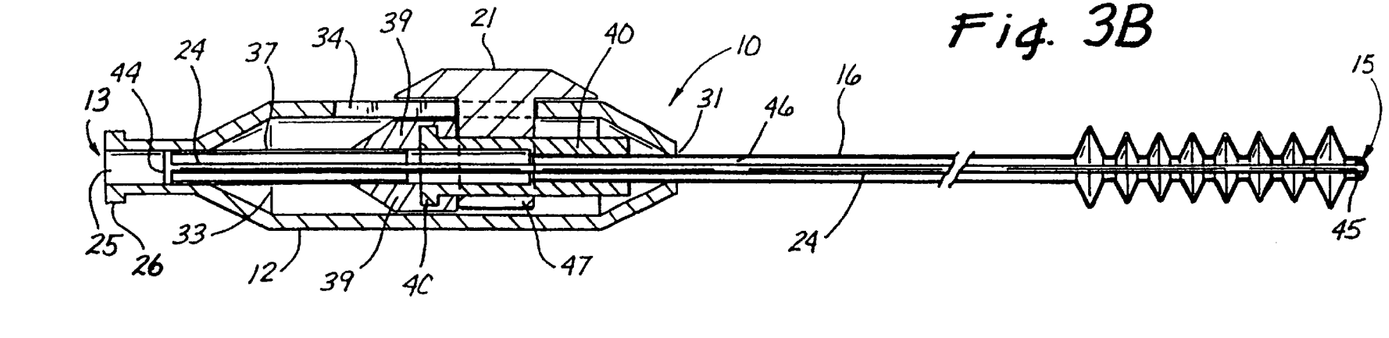
FIG. 3B is a cross-sectional view of the expandable intraluminal catheter in a deployed condition, according to the presently preferred embodiment.

Turning to FIGS. 3A and 3B, a cross-sectional view of the expandable intraluminal catheter 10 is illustrated in both a non-expanded and an expanded configuration, respectively. The elongate tubular body 16 fits through the aperture 31 in the handle 12 and extends through the handle 12 to the proximal end 13. A wire 24 fits within a lumen 46 of the elongate tubular body 16. The wire 24 is connected to a distal connection point 45 at the distal end 15 of the elongate tubular body 16, and is also connected at a proximal point 44 within the handle 12. The wire 24 maintains a relatively fixed distance between the handle 12 and the distal connection point 45. The actuator 21 slides within the slot 34 between the backward position (FIG. 3A) and the forward position (FIG. 3B). This actuator 21 comprises a portion 47 which extends into the handle 12. The portion 47 of the actuator 21 connects to a cylindrical bushing 40. The cylindrical bushing 40 is connected to the elongate tubular body 16, to thereby cause movement of the elongate tubular body 16 along the longitudinal axis of the elongate tubular body 16 with corresponding forward and reverse movement of the actuator 21 within the slot 34.

The cylindrical bushing 40 is connected at its proximal end to an elastomeric gasket or seal 39. A fixed tubular structure 37 is secured to the proximal point 44 at the handle 12. The cylindrical bushing 40 and the elastomeric gasket 39 slidably fit around the fixed tubular structure 37. Thus, movement of the actuator 21 from the reverse position (FIG. 3A) to the forward position (FIG. 3B) causes the bushing 40 and elastomeric gasket 39 to move along an outer surface of the fixed tubular structure 37 in the direction of movement of the actuator 21. The elastomeric gasket 39 maintains a seal between the lumen 46, which extends into the fixed tubular structure 37, and the general interior 33 of the handle 12. A watertight seal is thus formed from the opening 25, through the fixed tubular structure 37, elastomeric gasket 39, cylindrical bushing 40, and the elongate tubular body 16.

Figure 4A:
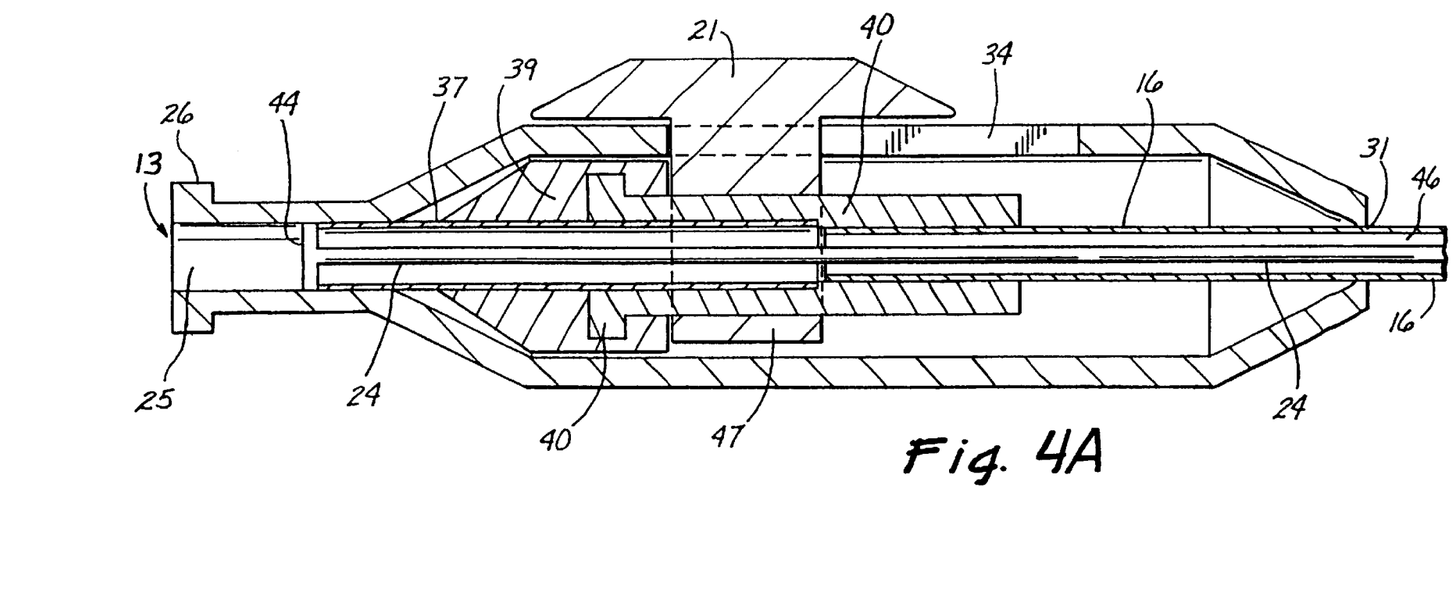
FIG. 4A is an enlarged axial cross-sectional view of the handle portion of the expandable intraluminal catheter in the position shown in FIG. 3A, according to the presently preferred embodiment.
Figure 4B:
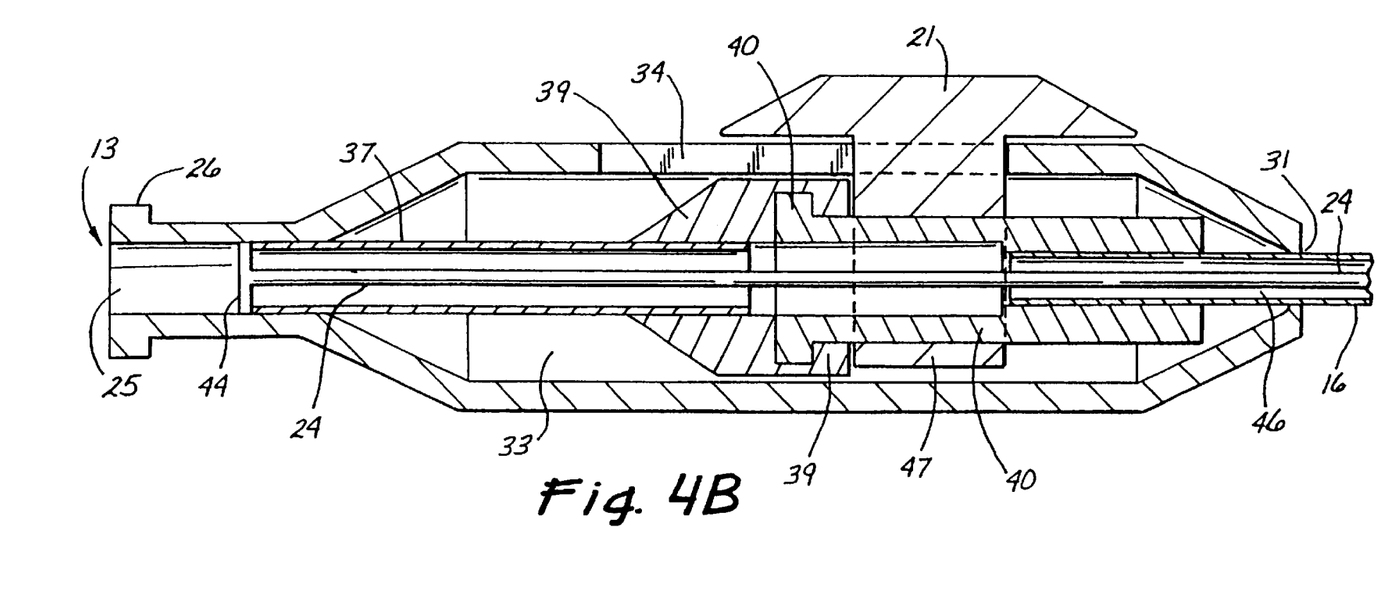
FIG. 4B is an enlarged axial cross-sectional view of the handle portion of the expandable intraluminal catheter in the position shown in FIG. 3B, according to the presently preferred embodiment.

Movement of the actuator 21 toward the distal end 15 moves the end of the elongate tubular body 16, which is attached to the cylindrical bushing 40, toward the distal end 15. Thus, movement of the actuator 21 toward the distal end 15 results in a corresponding movement of the proximal body end toward the distal body end 15. The distal body end 15 does not move forward with forward movement of the actuator 21, since the wire 24 maintains the distance between the distal body end 15 and the handle 12. The reduction in distance between the proximal body end and the distal body end 15 results in a compression of the segmented distal portion 14 from the relatively smooth, small-diameter configuration (FIG. 3A) to the larger diameter configuration (FIG. 3B). In other words, forward movement of the actuator 21 applies a compressive force to the segmented distal portion 14, which is relieved by expansion of the expandable segments 17, as the length of the expandable segments 17 decrease along the longitudinal axis of the elongate tubular body 16. FIGS. 4A and 4B are enlarged cross-sectional views of the handle 12 of FIGS. 3A and 3B, respectively.

Figure 5A:
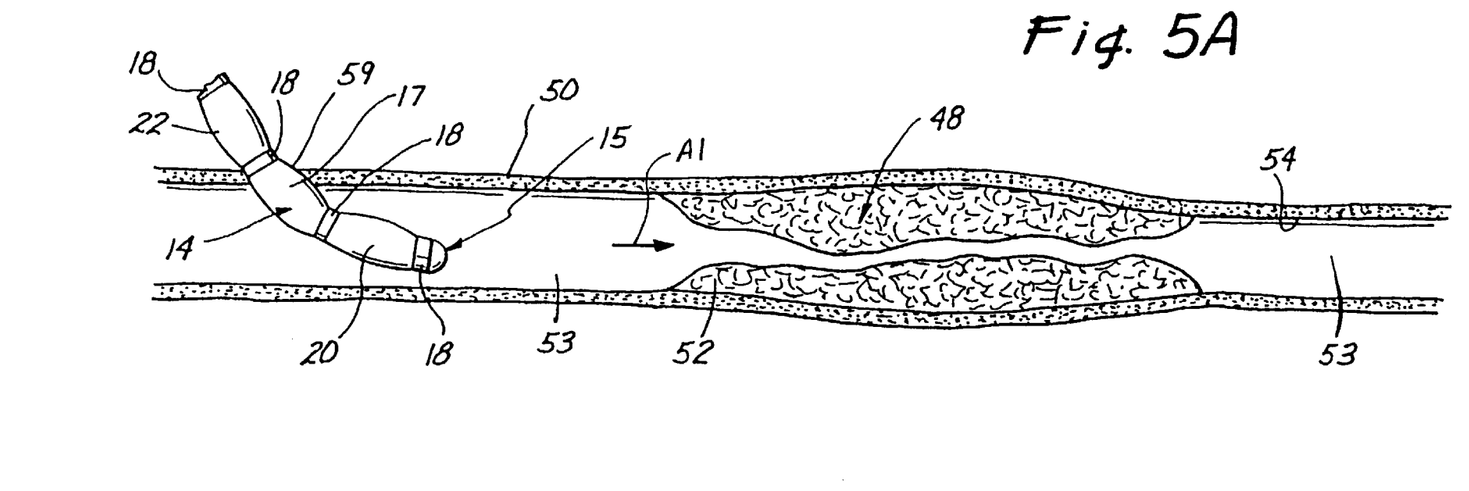
FIGS. 5A–5D are side-elevational views illustrating use of the expandable intraluminal catheter of the present invention to remove occlusive material from a body passage.
Figure 5B:
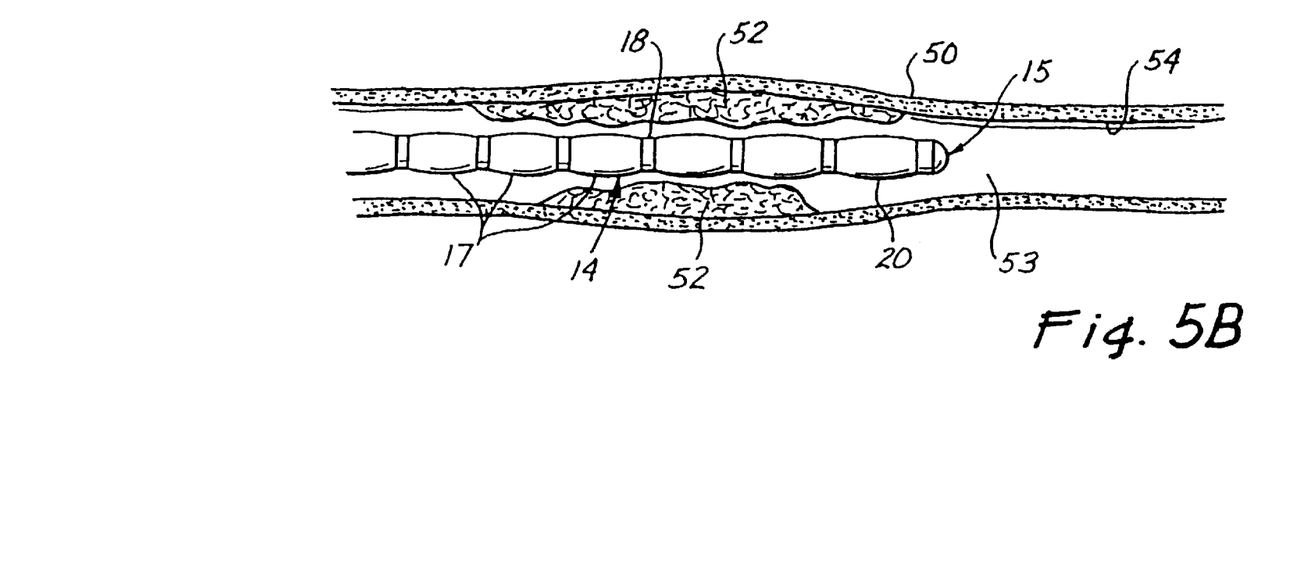
Figure 5C:
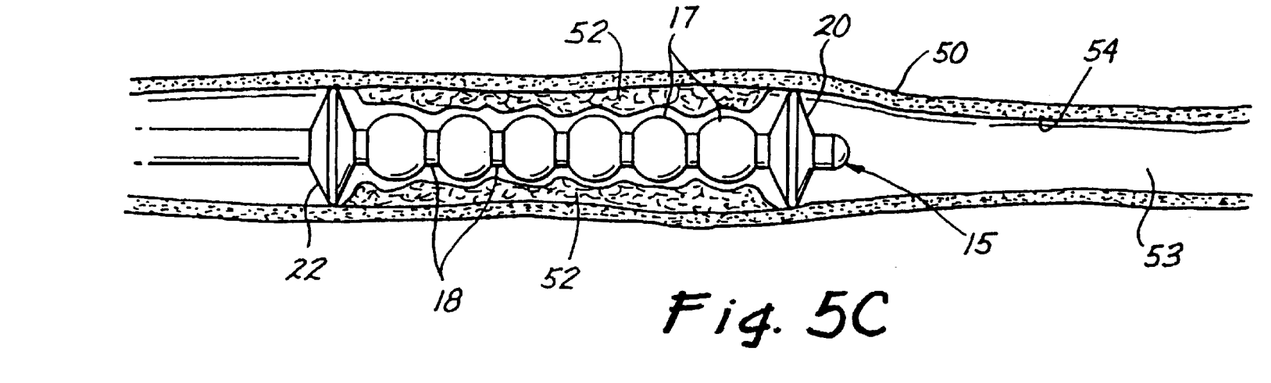
Figure 5D:
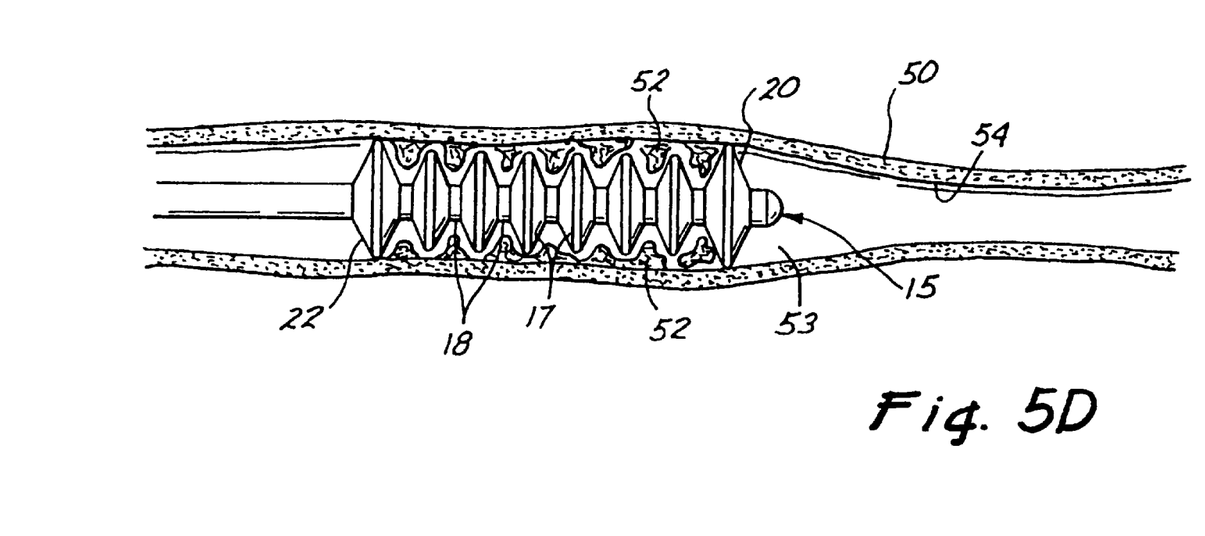

Turning to FIG. 5A, the segmented distal portion 14 of the elongate tubular body 16 is inserted through an incision or puncture 59 of a body passage 50. The body passage 50 may comprise a blood vessel, for example, having occlusive material 52 within the lumen 53 at an operation site 48. The occlusive material may be plaque, thrombi, emboli, or other potential clotting agents within the body passage 50. The segmented distal portion 14 is guided by the interior wall 54 of the body passage 50 to the operation site 48. As shown in FIG. 5B, the segmented distal portion 14 is inserted through the occlusive material 52 with relative ease, since the expandable segments 17 and the non-expandable segments 18 have relatively similar diameters and circumferences. The expandable segments 17 are mechanically activated by the actuator 21 to thereby radially expand, as shown in FIG. 5C. The distal expandable segment 20 and the proximal expandable segment 22 are preferably first radially expanded and, subsequently, the other radially-expanded segments on the segmented distal portion 14 are expanded. Thus, once the distal end 15 is moved in the direction of arrow A1 beyond the occlusive material 52, the expandable segments 17 are radially expanded by the compression force resulting from forward movement of the actuator 21. The expandable segments 17 isolate, mobilize, and capture the occlusive material 52 on a plurality of points along the interior wall 54.

The method of isolation, mobilization, and capture of the occlusive material 52 may be accomplished in several ways. Once the distal expandable segment 20 and the proximal expandable segment 22 are radially expanded, the other expandable segments 17 may be radially expanded and radially contracted to mechanically loosen the occlusive material 52 from the interior walls 54 of the body passage 50. Additionally, solvents or other medications may be administered through apertures formed in the expandable segments 17, excluding the expandable segment 20 and the proximal expandable segment 22. In an alternative embodiment, the expandable segment 20 and the proximal expandable segment 22 are not coated, and solvents, medications, etc. may be inserted and withdrawn from these segments 20, 22, as well. These fluids are inserted through the opening 25 (FIG. 1) of the expandable intraluminal catheter 10 and guided through the lumen 46 toward the segmented distal portion 14. A suction may be applied to the openings in the expandable segments 17 between the expandable segment 20 and the proximal expandable segment 22 to remove the chemically treated occlusive material 52. The occlusive material 52 may thus be aspirated, desiccated, or in other ways mechanically attached to the expandable segments 17 between the expandable segment 20 and the proximal expandable segment 22 by the negative internal pressure within the lumen 46. The distal expandable segment 20 and the proximal expandable segment 22, when expanded, substantially prevent solvents, medications, fluids, and other materials from escaping from the isolated treatment area defined between the distal expandable segment 20 and the proximal expandable coated segment 22. The distal expandable segment 20 and the proximal expandable segment 22 thus allow for localized treatment of the occlusive material 52, while preventing solvents, medications, fluids, and other materials including the occlusive material 52 from being administered systemically.

Figure 6A:
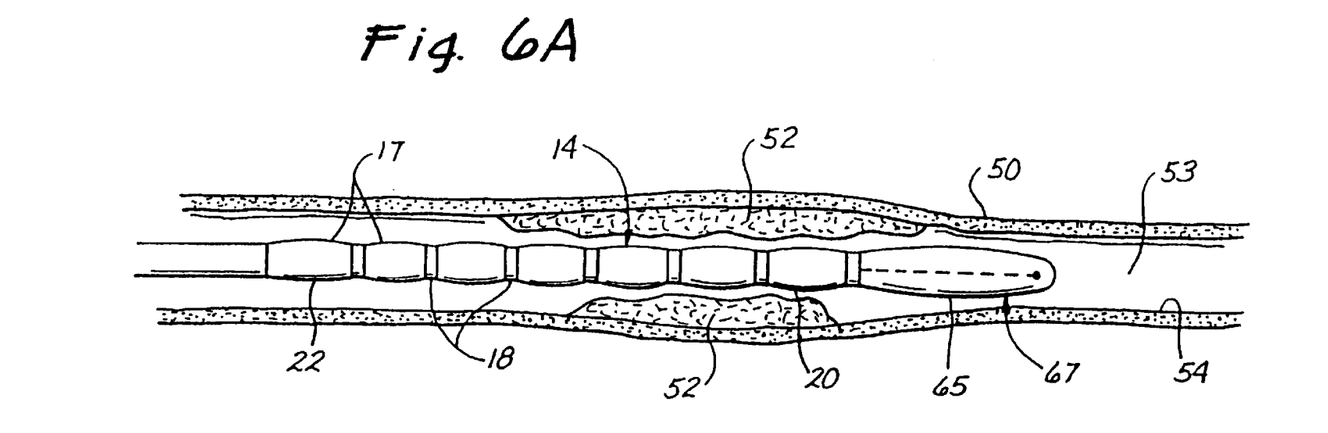
FIGS. 6A and 6B side elevation views of a further embodiment of the invention having a distal member comprising an elastomeric foam or a balloon.
Figure 6B:
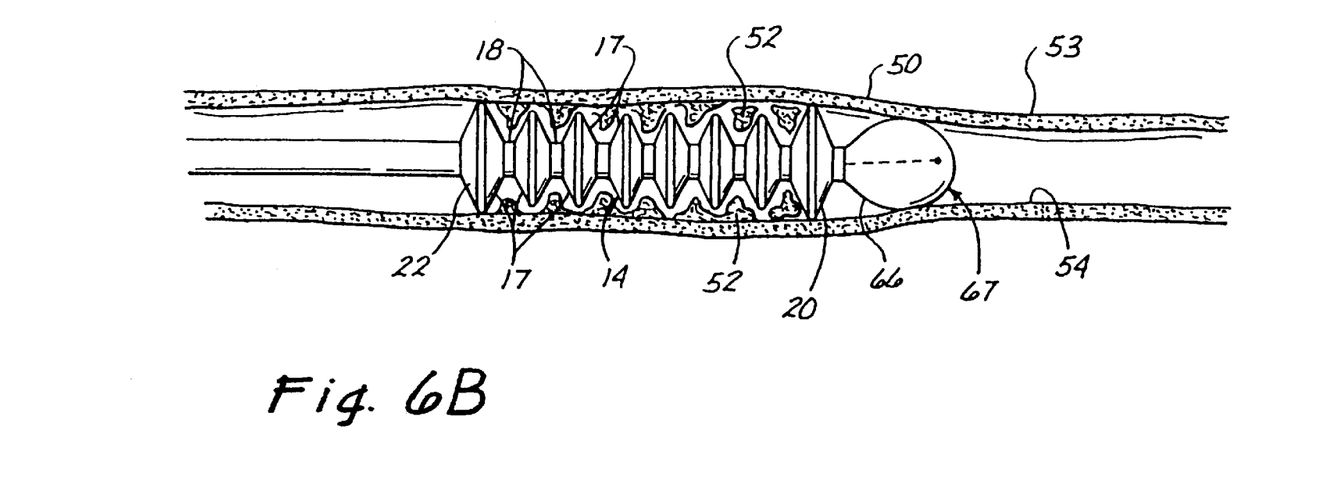

FIGS. 6A and 6B illustrate the expandable intraluminal catheter 10 according to an alternative embodiment. This configuration comprises an expandable-contractible distal member 67 of an elongated shape 65. When the actuator 21 is moved to the forward position, the distal member 67 is compressed into a generally spherical shape 66. This expandable-contractible distal member 67 preferably comprises an elastomeric foam, but a balloon may also be used. The action required to perform the stretching and compression of this expandable-contractible distal member 67 is the same action required to expand and contract the expandable segments 17. The expandable-contractible distal member 67 provides an additional function of further cleaning and removing small pieces of the occlusive material 52.

Although exemplary embodiments of the invention have been shown and described, many other changes, modifications and substitutions, in addition to those set forth in the above paragraph, may be made by one having ordinary skill in the art without necessarily departing from the spirit and scope of this invention.

What is claimed is:

1. An expandable intraluminal catheter for removing occlusive material from a body passage, comprising:

a handle;

an elongate tubular body coupled to the handle and having a lumen;

a plurality of expandable segments disposed on the elongate tubular body, the plurality of expandable segments comprising a proximal expandable segment, a distal expandable segment, and at least one intermediate expandable segment; and an actuator connected to the expandable segments and operable from the handle to actuate the plurality of expandable segments to radially expand, the distal expandable segment and the proximal expandable segment having a configuration different than that of the at least one intermediate expandable segment to facilitate expansion of the distal expandable segment and the proximal expandable segment to define a zone of treatment, and subsequently to facilitate expansion of the at least one intermediate expandable segment.

2. The expandable intraluminal catheter as recited in claim 1, the expandable intraluminal catheter further comprising:

a non-expandable member disposed within the lumen of the elongate tubular body, the non-expandable member having a proximal non-expandable member end and a distal non-expandable member end;

the handle having a proximal handle end and a distal handle end;

the elongate tubular body having a proximal body end, a distal body end, with the lumen extending between the proximal body end and the distal body end;

the proximal body end being connected to the distal handle end and the plurality of expandable segments being disposed on the elongate tubular body near the distal body end;

the proximal non-expandable member end being connected to the proximal handle end, and the distal non-expandable member end being connected to the distal body end, the connection of the non-expandable member between the proximal handle end and the distal body end holding the distal non-expandable member end relatively stationary with regard to the proximal handle end; and the actuator being connected to the proximal body end to radially expand the plurality of expandable segments by moving the proximal body end toward the relatively stationary distal body end, and to radially contract the plurality of expandable segments by moving the proximal body end away from the relatively stationary distal body end.

3. The expandable intraluminal catheter as recited in claim 1, wherein each of the plurality of expandable segments comprises one of a tubular woven, a tubular braided, and a tubular meshed material, and wherein apertures are formed on each of the plurality of expandable segments, upon expansion of the segments by the actuator, to thereby allow for application of one of a pressure and a suction through both the lumen and the apertures.

4. The expandable intraluminal catheter as recited in claim 3, wherein each of the proximal expandable segment and the distal expandable segment comprises a coating of non-permeable dispersion coating.

5. The expandable intraluminal catheter recited in claim 1 wherein the distal expandable segment and the proximal expandable segment have a first diameter in an expanded state, and the at least one intermediate expandable segment has a second diameter less than the first diameter in the expandable state, to facilitate expansion of the distal expandable segment and the proximal expandable segment prior to expansion of the at least one intermediate expandable segment.

6. An expandable intraluminal catheter for removing occlusive material from a body passage, comprising:

an elongate tubular body having a length extending between a proximal body end and a distal body end;

a plurality of expandable segments disposed on the elongate tubular body near the distal body end, the plurality of expandable segments comprising a proximal expandable segment, a distal expandable segment, and at least one intermediate expandable segment;

an actuator having a generally fixed position with respect to one of the proximal body end and the distal body end, and being operable from the generally fixed position to move the other of the proximal body end and the distal body end to alternatively increase and decrease the length of the elongate tubular body; and the distal expandable segment and the proximal expandable segment having a configuration facilitating expansion of the distal expandable segment and the proximal expandable segment prior to expansion of the at least one intermediate expandable segment.

7. The expandable intraluminal catheter recited in claim 6 wherein the distal expandable segment and the proximal expandable segment have a first diameter in an expanded state, and the at least one intermediate expandable segment has a second diameter less than the first diameter in the expandable state, to facilitate expansion of the distal expandable segment and the proximal expandable segment prior to expansion of the at least one intermediate expandable segment.

8. An expandable intraluminal catheter for removing occlusive material from a body passage, comprising:

an elongate tubular body having a proximal body end, a distal body end, and a variable length between the proximal body end and the distal body end;

a distal expandable segment disposed on the elongate tubular body near the distal body end, the distal expandable segment having a first length in a non-expanded state;

at least one intermediate expandable segment disposed on the elongate tubular body proximally of the distal expandable segment, the at least one intermediate expandable segment having a second length in a non-expanded state; and a proximal expandable segment disposed on the elongate tubular body proximally of the intermediate expandable segment, the proximal expandable segment having a third length in a non-expanded state, the first length being greater than the second length, and the third length being greater than the second length.

9. The expandable intraluminal catheter as recited in claim 8, wherein:

the proximal expandable comprises a coating of non-permeable dispersion material, and the distal expandable segment comprises a coating of non-permeable dispersion material.

10. The expandable intraluminal catheter as recited in claim 7, further comprising a plurality of non-expandable segments, the distal expandable segment, the at least one intermediate expandable segment, and the proximal expandable segment being separated by a corresponding plurality of non-expandable segments, each of the plurality of non-expandable segments being disposed adjacent to at least one of the expandable segments on the elongate tubular body.

11. The expandable intraluminal catheter as recited in claim 10, further comprising an actuator coupled to the elongate tubular body and operable to vary the length of the elongate tubular body to actuate the expandable segments and thereby cause, by means other than inflation, the expandable segments to radially expand into semi-rigid enlarged-diameter segments by decreasing the length of the elongate tubular body and to radially contract the semi-rigid enlarged-diameter segments by increasing the length of the elongate tubular body.

12. The expandable intraluminal catheter as recited in claim 11, wherein:

a length of the first expandable segment, a length of the second expandable segment, and a length of the third expandable segment are attenuated as the expandable segments radially expand, and the lengths of the non-expandable segments are not attenuated as the expandable segments radially expand.

13. The expandable intraluminal catheter as recited in claim 11, wherein the expandable segments and the corresponding non-expandable segments are integrally formed with the exterior surface of the elongate tubular body, each expandable segment being joined to an adjacent non-expandable segment at a bendable joint.

14. The expandable intraluminal catheter as recited in claim 13, wherein:

each of the plurality of expandable segments comprising an expandable, plastic, tubular braid; and each of the corresponding plurality of non-expandable segments comprising a semi-rigid plastic tubing.

15. The expandable intraluminal catheter as recited in claim 14, wherein:

the proximal expandable segment comprises a coating of non-permeable dispersion material; and the distal expandable segment comprises a coating of non-permeable dispersion material.

16. The expandable intraluminal catheter as recited in claim 15, further comprising:

a handle having a proximal handle end and a distal handle end; and a wire coupled to the handle and the elongate tubular body for maintaining the distal body end and the proximal handle end in a generally fixed relationship.

17. The expandable intraluminal catheter as recited in claim 16, wherein:

the elongate tubular body has a lumen along the length of the elongate tubular body, the lumen accommodating the wire; and the actuator is connected to the proximal body end, the actuator actuating the expandable segments to radially expand by moving the proximal body end toward the distal body end, the actuator actuating the plurality of expandable segments to radially contract by moving the proximal elongate tubular end away from the distal body end, while the wire maintains a constant distance between the proximal handle end and distal body end.

18. The expandable intraluminal catheter as recited in claim 7, wherein apertures are formed on the at least one intermediate expandable segment, upon expansion of the at least one intermediate expandable segment, to thereby allow for application of one of a pressure and a suction to the apertures, and wherein one of a pressure and a suction can be applied to the apertures through the elongate tubular body.

19. The expandable intraluminal catheter as recited in claim 18, further comprising a handle coupled to the elongate tubular body and having a port in the handle comprising a luer type locking hub that is adapted to allow fluid to be inserted into the elongate tubular body and to be excreted through the apertures, the luer type locking hub further being adapted to allow fluid to be drawn through the apertures and out of the elongate tubular body.

20. The expandable intraluminal catheter as recited in claim 7, further comprising:

an expandable distal member, located on the elongate tubular member between the distal body end and the expandable segments; and a non-expandable member disposed within the elongate tubular body and having a distal non-expandable member end which is connected to the distal body end, the non-expandable member being coupled to the actuator and cooperating with the actuator to vary the length of the tubular member.

21. The expandable intraluminal catheter as recited in claim 20, wherein the expandable distal member comprises an elastomeric foam, which, when expanded by the non-expandable member, is deformable from an elongated shape into a generally spherical shape.

22. The expandable intraluminal catheter as recited in claim 20, wherein the expandable distal member comprises an inflatable balloon, which, when inflated, is deformable from an elongated shape into a generally spherical shape.

* * * * *